US009032370B2

(12) United States Patent
Chakraborty et al.

(10) Patent No.: US 9,032,370 B2
(45) Date of Patent: May 12, 2015

(54) AUTOMATED TEST CYCLE ESTIMATION SYSTEM AND METHOD

(71) Applicant: Tata Consultancy Services Limited, Maharashtra (IN)

(72) Inventors: Soham Sundar Chakraborty, West Bengal (IN); Pavan Kumar Chittimalli, Pune (IN); Vipul Shah, Pune (IN)

(73) Assignee: Tata Consultancy Services Limited (IN)

( * ) Notice: Subject to any disclaimer, the term of this patent is extended or adjusted under 35 U.S.C. 154(b) by 204 days.

(21) Appl. No.: 13/719,568

(22) Filed: Dec. 19, 2012

(65) Prior Publication Data
US 2013/0174178 A1    Jul. 4, 2013

(30) Foreign Application Priority Data

Dec. 29, 2011    (IN) .......................... 3698/MUM/2011

(51) Int. Cl.
*G06F 9/44*    (2006.01)
*G06F 11/36*    (2006.01)
*G06F 9/46*    (2006.01)
*G06F 9/50*    (2006.01)

(52) U.S. Cl.
CPC .............. *G06F 11/3672* (2013.01); *G06F 9/46* (2013.01); *G06F 9/5066* (2013.01)

(58) Field of Classification Search
USPC ..................................... 717/124; 714/40, 809
See application file for complete search history.

(56) References Cited

U.S. PATENT DOCUMENTS

| 6,587,811 | B2 * | 7/2003 | Schleifer et al. ............. 702/176 |
| 7,080,351 | B1 | 7/2006 | Kirkpatrick et al. |
| 7,305,654 | B2 * | 12/2007 | Patel et al. .................... 717/101 |
| 7,480,900 | B1 * | 1/2009 | Zhou et al. .................... 717/132 |
| 7,913,230 | B2 * | 3/2011 | Vikutan ......................... 717/124 |
| 8,132,056 | B2 * | 3/2012 | Thakkar et al. .............. 714/38.1 |
| 8,458,662 | B2 * | 6/2013 | Grechanik et al. ............ 717/124 |
| 8,683,442 | B2 * | 3/2014 | Peranandam et al. ........ 717/124 |
| 8,799,868 | B2 * | 8/2014 | Ndem et al. .................. 717/126 |
| 2003/0163297 | A1 * | 8/2003 | Khaira et al. .................. 703/15 |
| 2005/0102594 | A1 * | 5/2005 | Dey et al. ...................... 714/733 |
| 2005/0222885 | A1 | 10/2005 | Chen et al. |
| 2005/0223361 | A1 * | 10/2005 | Belbute ......................... 717/124 |

(Continued)

OTHER PUBLICATIONS

Integrating Physical Constraints in HW-SW Partitioning for Architectures With Partial Dynamic Reconfiguration—Sudarshan Banerjee, Member, IEEE, Elaheh Bozorgzadeh, Member, IEEE, and Nikil D. Dutt, Senior Member, IEEE—IEEE Transactions on Very Large Scale Integration (VLSI) Systems, vol. 14, No. 11, Nov. 2006.*

(Continued)

*Primary Examiner* — Lewis A Bullock, Jr.
*Assistant Examiner* — Francisco Aponte
(74) *Attorney, Agent, or Firm* — Thompson Hine LLP

(57) ABSTRACT

A system and method is disclosed to estimate both, the time and number of resources required to execute a test suite or a subset of test suite in parallel, with the objective of providing a balanced workload distribution. The present invention partitions test suite for parallelization, given the dependencies that exists between test cases and test execution time.

15 Claims, 11 Drawing Sheets

(56) References Cited

U.S. PATENT DOCUMENTS

| | | | |
|---|---|---|---|
| 2007/0198971 A1* | 8/2007 | Dasu et al. | 717/140 |
| 2008/0256392 A1* | 10/2008 | Garland et al. | 714/33 |
| 2009/0287963 A1* | 11/2009 | Oglesby et al. | 714/38 |
| 2010/0251204 A1* | 9/2010 | Peterson et al. | 717/102 |
| 2011/0066490 A1* | 3/2011 | Bassin et al. | 705/14.48 |
| 2011/0145653 A1* | 6/2011 | Broadfoot et al. | 714/38.1 |
| 2011/0258602 A1* | 10/2011 | Ndem et al. | 717/124 |
| 2013/0086434 A1* | 4/2013 | Bhamidipaty et al. | 714/48 |

OTHER PUBLICATIONS

Integrating Physical Constraints in HW-SW Partitioning for Architectures With Partial Dynamic Reconfiguration Sudarshan Banerjee, Member, IEEE, Elaheh Bozorgzadeh, Member, IEEE, and Nikil D. Dutt, Senior Member, IEEE—IEEE Transactions on Very Large Scale Integration (VLSI) Systems, vol. 14, No. 11, Nov. 2006.*

Yves Le Traon & Benoit Baudry "Optimal Allocation of Testing Resources," http://people.rennes.inria.fr/Benoit.Baudry/ (published at least as early as Dec. 12, 2012).

* cited by examiner

AUTOMATED TEST CYCLE ESTIMATION SYSTEM AND METHOD

FIELD OF THE INVENTION

The present invention generally relates to the field of software test estimation and, more particularly, to automated test cycle estimation for parallel execution of test cases during software testing.

BACKGROUND OF THE INVENTION

Business applications under maintenance are in a constant state of change to keep pace with the changing business requirements. This results in frequent releases of the software system. An important task in the maintenance process is therefore to test the new or modified functionality and to ensure that the rest of the system unaffected by the change does not break down. Functional tests to test the changes and regression tests are executed multiple times in each test cycle. Test teams are therefore under constant pressure to reduce test cycle time, and with low test automation levels to make optimal use of available resources. Adding more resources to parallelize testing so as to reduce time, does not always help as dependencies may exist between test cases that mandate an order for test execution. The number of test cases and the test cases themselves may vary in each test cycle making accurate time and effort estimation for test cycle a challenge.

Within each release cycle, the time taken for testing and resources are estimated from the available time and efforts, using empirical data and experience. This is computed statically for each release cycle. Very little effort has been directed towards addressing dynamic time and resource estimation and arriving at effective workload distribution during test cycle.

The parallel execution of test cases results in out of order operations on the system. In such a case, if test cases use persistent data source, for example, a database across the test cases, then different execution sequences might result in different output due to the dependencies across the test cases. The impact of execution sequences of the test cases has been identified in the past where the test cases have been partitioned based on state preservation by resetting the states. The work done in the prior art creates a conflict database for out of order executions and analyzes the same to reorder test sequences. The approach assumes automation and its applicability and effectiveness for manual testing has to be studied. The experts, in the past, have used static analysis to analyze the dependencies across the JDBC queries in a program. The approach assumes that testers have full access to the systems and the source code which is often not the case in most of the projects during functional and regression test cycles.

Parallel and distributed executions of test cases are explored and used in various tools and frameworks. In these frameworks testers specify the test cases that can run in parallel. Previously, authors have proposed a framework to execute the regression test cases in a distributed manner and also some of the previous works has also shown execution of test cases in parallel and in a distributed manner on the cloud framework.

The distributions of test cases may result from different reasons such as functionality, domain understanding etc. One of the works of the prior art partitions the test cases which capture related set of bugs by analyzing the source code. However, in this case the test cases are independent and they consider the source code availability. Some have even considered resource constraints as the parameter of test suite distribution. But no one has ever considered dependencies across test cases as the constraint to be handled during workload distribution.

Further, various approaches have been discussed to achieve balanced partitions. Also, time aware test case execution schemes have also been discussed where prioritization of test cases for a given constraint is taken care of. None of the arts have identified the resource requirement for the specified time constraint.

In the view of above technical challenges an automated approach to partition the test suite for parallelization given the dependencies existing between the test cases is what is needed as a technical solution.

OBJECTIVES OF THE INVENTION

The principle object of the present invention is to provide a system and method for estimating both time and resources required to execute a test suite or subset of test suite in parallel with the objective of providing a balanced workload distribution.

Another significant object of the invention is to generate an estimation technique that can determine the number of changes that can be incorporated in a release of the software system.

It is another object of the present invention to enable the test team to estimate the resource requirement to complete each test cycle within specified deadline.

Another object of the invention is to enable the test team to estimate the amount of time it would take to complete the test cycle with given number of resources.

Yet another object of the invention is to provide a scheme for effective workload distribution for improved resource utilization during test cycle execution.

SUMMARY OF THE INVENTION

Before the present methods, systems, and hardware enablement are described, it is to be understood that this invention is not limited to the particular systems, and methodologies described, as there can be multiple possible embodiments of the present invention which are not expressly illustrated in the present disclosures. It is also to be understood that the terminology used in the description is for the purpose of describing the particular versions or embodiments only, and is not intended to limit the scope of the present invention which will be limited only by the appended claims.

The present invention envisages a system and method for dynamic time and resource estimation required to execute plurality of test cycles in parallel, with the objective of providing a balanced workload distribution.

In the preferred embodiment of the invention a computer implemented method of constraint estimation during execution of plurality of test cycle is provided wherein the method is having a computer executable code tangibly embodied on a computer readable storage medium and comprises of the following steps: receiving the constraints determining execution of the test cycles, a set of test cases in the each test cycle and one or more test cases selected from the set of test cases; constructing a first associated dependence graph for the test cases and a second dependence sub graph for the selected test cases within the each test cycle for determining one or more corresponding disconnected components and the associated component weights; performing balanced distribution of the identified disconnected components across one or more partition based on the received constraint such that difference between maximum and minimum weighted partitions is minimal for resource as a constraint, and the partitions are executed within a given time for time as a constraint; and computing estimation efficiency of the constraints based on the created partitions.

One of the other preferred embodiments of the present invention presents a constraint estimation system for executing plurality of test cycles in a dynamic environment, the system comprising: an input module for receiving the constraints determining execution of the test cycles, a set of test cases in the each test cycle and one or more test cases selected from the set of test cases; a dependency module configured to collaborate with the input module for extracting associated dependence and generating first associated dependence graph for the test cases and a second dependence sub graph for the selected test cases within the each test cycle for determining one or more corresponding disconnected components; and a partitioner adapted to perform balanced distribution of the identified disconnected components across one or more partitions based on the received constraint such that difference between maximum and minimum partitions is minimal for resource as a constraint, and the partitions are executed within a given time for time as a constraint.

BRIEF DESCRIPTION OF THE DRAWINGS

The foregoing summary, as well as the following detailed description of preferred embodiments, are better understood when read in conjunction with the appended drawings, wherein like elements are given like reference numerals. For the purpose of illustrating the invention, there is shown in the drawings example constructions of the invention; however, the invention is not limited to the specific methods and system disclosed. In the drawings.

DETAILED DESCRIPTION OF THE INVENTION

Figure 1:
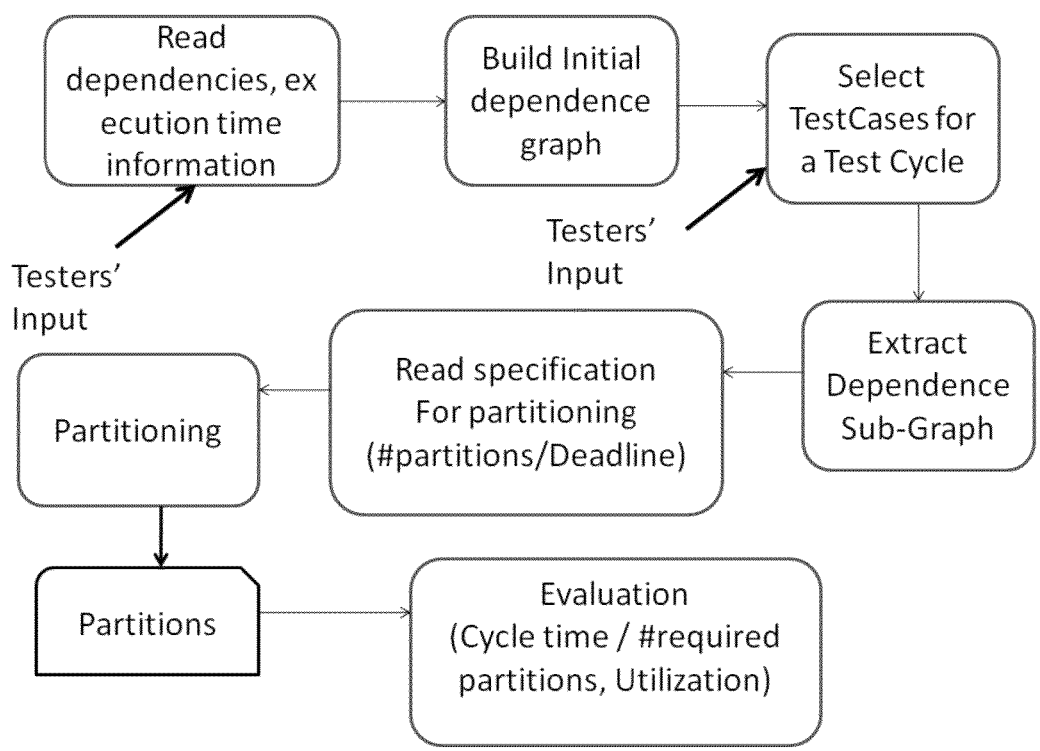
FIG. 1 is a flow diagram showing steps of estimating the constraints for test cycle execution in accordance with a preferred embodiment of the present invention.

Some embodiments of this invention, illustrating all its features, will now be discussed in detail.

The words "comprising," "having," "containing," and "including," and other forms thereof, are intended to be equivalent in meaning and be open ended in that an item or items following any one of these words is not meant to be an exhaustive listing of such item or items, or meant to be limited to only the listed item or items.

It must also be noted that as used herein and in the appended claims, the singular forms "a," "an," and "the" include plural references unless the context clearly dictates otherwise. Although any systems and methods similar or equivalent to those described herein can be used in the practice or testing of embodiments of the present invention, the preferred, systems and methods are now described.

The disclosed embodiments are merely exemplary of the invention, which may be embodied in various forms. Software programming code, which embodies aspects of the present invention, is typically maintained in permanent storage, such as a computer readable medium. In a client-server environment, such software programming code may be stored on a client or a server. The software programming code may be embodied on any of a variety of known media for use with a data processing system. This includes, but is not limited to, magnetic and optical storage devices such as disk drives, magnetic tape, compact discs (CD's), digital video discs (DVD's), and computer instruction signals embodied in a transmission medium with or without a carrier wave upon which the signals are modulated. For example, the transmission medium may include a communications network, such as the Internet. In addition, while the invention may be embodied in computer software, the functions necessary to implement the invention may alternatively be embodied in part or in whole using hardware components such as application-specific integrated circuits or other hardware, or some combination of hardware components and software.

Definitions a) Test Case: A test case, TC, tests for a specific functionality and is considered atomic.

b) Test Suite: Test Suite, TS, is a set of test cases TS={$TC_1$; $TC_2$; : : : ; $TC_n$} c) Component: A component is an ordered set of test cases.

d) Partition: A partition is a set of components that satisfy given constraints.

In the maintenance phase, business applications go through a constant state of change to keep pace with changing business requirements. The maintenance of business applications is in fact an evolutionary development. A large part of the maintenance primarily involves adding a new functionality or modifying an existing functionality as against bug fixes. An important task in the maintenance process is therefore to test the new or modified functionality and to ensure that the rest of the system unaffected by the change does not break down. The resource requirement estimation, workload distribution and task assignment, are common activities in regular project management. Continuous changes result in frequent releases of the software system. Release cycles are usually fixed and the frequency of release is decided based on the number of releases planned apriori. Estimation techniques are then used to determine the number of changes that can be incorporated in a release. Empirical data is often used to estimate test efforts which are more often than not computed as a percentage of the total effort.

As the release cycles vary from several weeks to several months, changes are grouped together for testing in a test cycle. It is a common practice to have multiple test cycles as part of each release cycle with each test cycle having a combination of functional tests to test a set of changes and as well as tests that failed earlier. In order to complete the test cycles within the given deadline and to achieve coverage target on regression suite, test teams resort to running a subset of regression tests for each test cycle, running the complete regression suite only at fixed intervals. Therefore every test cycle is likely to have a different test execution plan.

Studies conducted on approximately 900 projects have revealed that about 80% test projects follow a manual testing process, making it a resource intensive activity. To optimize the number of resources and deliver within the stipulated deadline, test teams need to parallelize test execution for the subset of test cases selected. The terms "resources" and "testers" is synonymously used for the purposes of present invention.

The task to estimate resources needed for test cycles and distribution of workload amongst them is nontrivial due to following reasons:
- a) Productivity of a tester depends on the familiarity of the tester with the domain and possibly the application. This has an impact on the number of resources that can be deployed for a test cycle as well as the test cases that can be assigned to a tester.
- b) The test team size varies from time to time and hence a one-time workload distribution does not suffice for all test cycles. Based on the number of resources the workload has to be dynamically distributed for effective utilization of resources.
- c) Different changes result in different execution of subsets. The number of test cases and the test cases themselves therefore vary across test cycles.
- d) Perhaps the most important reason is that there exist dependencies among the test cases and the test cases need to be executed in a particular sequence. Out of order executions of the dependent test cases could lead to incorrect results.

Considering all the above, especially the dependencies, it requires an involved effort to come up with accurate estimation of test cycle and workload distribution. Computing it manually especially under stipulated deadlines is a difficult task. Thus, is established the need for a system that can help test teams to estimate and plan the tests cycles better, and improve resource utilization thereby making the test teams more predictable.

In the present invention, a system and method to partition test suite for parallelization, given the dependencies that exists between test cases and test execution time, is provided. The system and method partitions test suite taking into account either time or resource constraints. Test teams can provide constraints in terms of number of available resources or the deadline and get a workload distribution that satisfies the constraints and is balanced at the same time. The resulting work execution plans aid test cycle estimation. The impact of changing time and resource constraints on test cycle estimates is also provided.

Given test case dependencies and test execution time, for a test selection, a dependence graph is constructed based on the ordering amongst the selected test cases. Disconnected components are identified in the graph and balanced partitions are created for the given time or resource constraints. Providing the dependence information is a one-time activity and needs to be changed when the dependence or the execution time changes or when new test cases are added.

Referring now to FIG. 1, the procedural steps for executing the present invention is provided in the form of a flow diagram. The approach has been detailed here below to enable the person skilled in the art to perform the present invention without any undue experimentation.

A) Firstly, the input specifications received are as follows:
For each test case, a list of test cases that the current test case is dependent on before it can be executed and the total time it takes for execution.
For each test cycle the specified inputs are
- a. A set of selected test cases, that is the entire set and/or the subset of test cases in the test suite to be executed as per the changes to be test in the given cycle.
- b. The resource availability, that is, the number of testers available for the test cycle or
- c. The deadline for the test cycle that is the time constraint.

The above mentioned information is used for test execution plan generation and evaluation.

B) Now a dependence graph is constructed using the specified input: The test cases in the test suite are modeled as a directed graph $G=\{V; E\}$ where V is the set of vertices and E is the set of edges. An edge $e \in E$ between the vertices pair $<v_1, v_2>$ represents that the execution of test node $v_2$ must happen after the execution of test node $v_1$. It is assumed that there exist no cyclic dependencies across the test cases and hence G is either a tree or a directed acyclic graph (DAG).

For each test node $v \in V$, a weight $W_v$ is assigned. $W_v$ denotes the execution time of the test case. For example, a dependence graph for a set of test cases $\{TC_1; TC_2; :::; TC_{15}\}$ along with respective weights is as shown in FIG. 2.

C) Constructing a Dependence Sub-graph from the dependence graph—For the subset of the test cases $\{TC_1; :::; TC_k\}$ selected in a test cycle, dependence sub-graph G' is extracted from the original dependence graph G. G' is obtained by performing a depth first walk on G, starting from each of the selected nodes, including the test cases dependent on the selected nodes.

Figure 2:
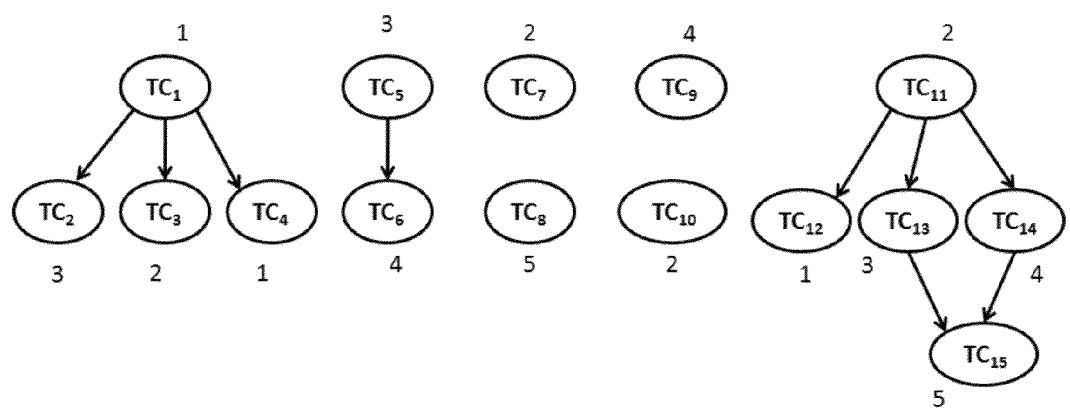
FIG. 2 shows the first dependence directed graph constructed for the test cases in accordance with one of the embodiments of the present invention.
Figure 3:
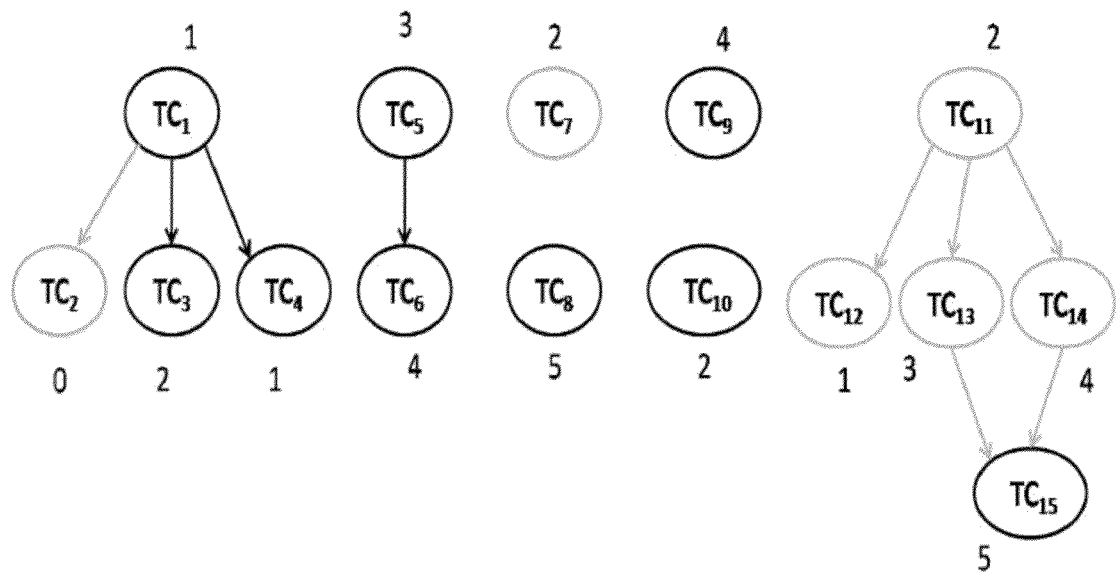
FIG. 3 represents the selected test cases in dependence graph in accordance with one disclosed embodiment of the present invention.
Figure 4:
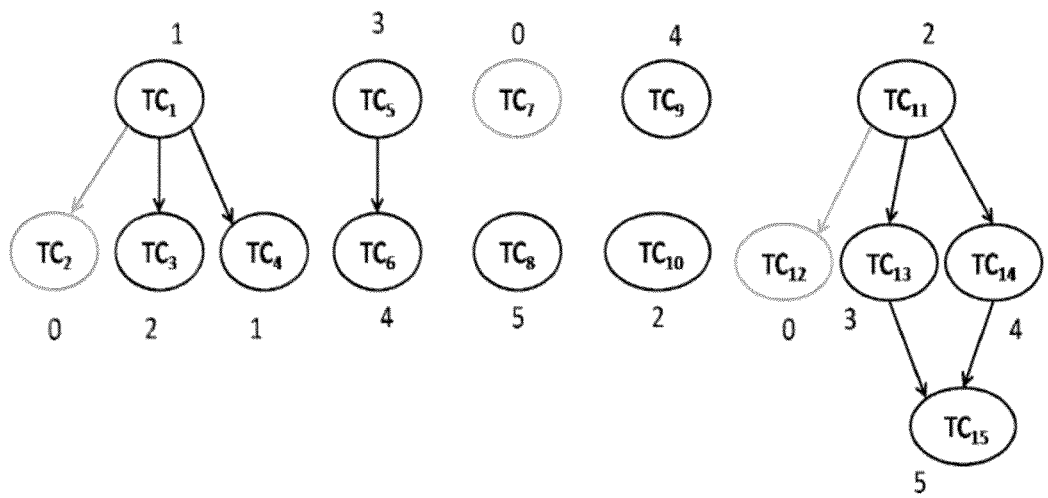
FIG. 4 shows the second sub-dependence graph as extracted from the first dependence graph in accordance with a disclosed embodiment of the invention.

For example considering a set of selected nodes, as shown in FIG. 3, comprising of $\{TC_1, TC_3, TC_4, TC_6, TC_6, TC_8, TC_9, TC_{10}, TC_{15}\}$ from the initial dependence graph shown in FIG. 2. Then the selected set of test cases is $\{TC_1, TC_3, TC_4, TC_5, TC_6, TC_8, TC_9, TC_{10}, TC_{11}, TC_{13}, TC_{14}, TC_{15}\}$ are selected. No test case is dependent upon test case $TC_2$, $TC_7$ and $TC_{12}$. Hence they are not in G'. Test cases $TC_{15}$ depends on test cases $TC_{13}$ and $TC_{14}$ which in turn depend on $TC_{11}$. Hence all 3 are selected as shown in FIG. 4.

The execution dependencies across the test cases result in partial orderings across the executions of the test cases in the test suite. If the dependent test events are distributed across different testers or computing resources then the test events may be executed independently in an out-of-order sequence and would result in an undesired output. To avoid this, a set of dependent test events is grouped together and assigned to a single tester which would ensure the execution ordering. It corresponds to identifying the disconnected components in the dependence graph G'.

D) Identifying Disconnected Components: In the graph, for a subset of nodes, if there exist no incoming or outgoing edges to other nodes in the graph then the subset of nodes is considered as a component. For example, in FIG. 2, $\{TC_3; TC_4; TC_5\}$ form a component which is disconnected from other nodes in the graph. The disconnected components in the directed graph are identified by the following given algorithm:

Algorithm 1 Disconnected Component Identification

Require: G' = {V,E}: Dependence Graph of Test cases. Array
  tcList : Set of Test cases in G'.
Ensure: compList: List of Disconnected Components in G'.
  BEGIN
  for all Test case tc ∈ tcList do
    if tc is unvisited then
      mark tc as visited;
      Create new Component C, contains a set of test cases;
      C ⇐ C ∪ {tc};
      for all Test case tc' do
        if < tc,tc' > ∈ E or < tc',tc > ∈ E then
          mark tc' as visited;
          C ⇐ C ∪ {tc'};
        end if
      end for
    end if
  end for
  END The execution of test cases across the different components does not require any ordering. Each disconnected component can be considered as independent partition and the components may run in parallel. The weight of a component is the accumulation of the weights of the test case nodes in that component. If a component C includes the test cases $\{TC_1; TC_2; ::::; TC_n\}$ then the component's weight $$W_c = \sum_{i=1}^{n} W_{Tc_i}$$

Figure 5:
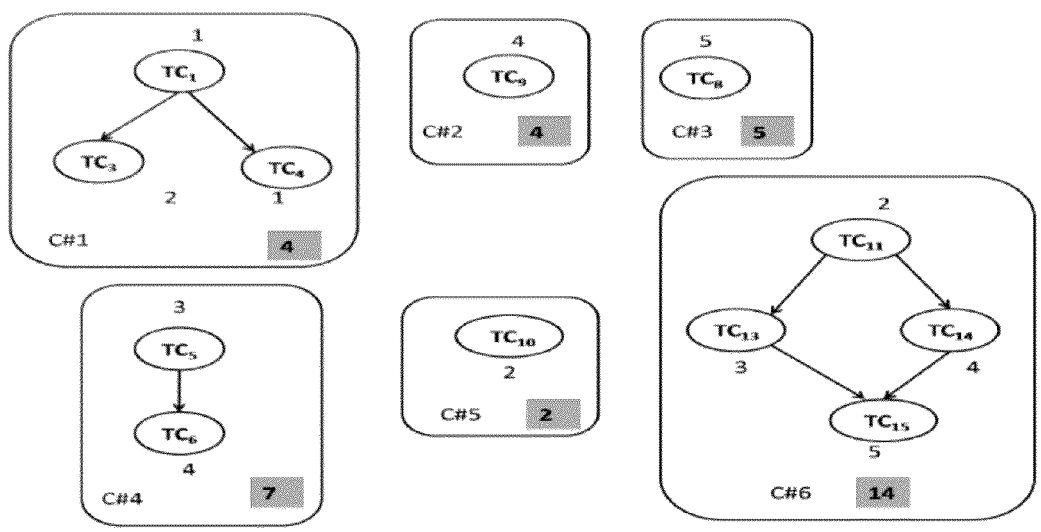
FIG. 5 is a representation of identified disconnected components in accordance with a disclosed embodiment of the present invention.

FIG. 5 highlights the identified disconnected components from FIG. 3 along with their weights.

E) Partitioning and Workload Distribution: A resource can be assigned to test each component in parallel. The total test execution time would then be the same as the maximum weight among the components. Components could differ in sizes leading to under utilization of resources. The workload of each tester is therefore required to be balanced. The disconnected components are considered as atomic units for workload distribution. The workload distribution is driven in two ways—(i) If the resource availability is known then the workload for each tester or resource has to be identified (ii) the execution time is specified and the number of resources required has to be identified for a balanced workload distribution. The techniques of partitioning are as follows.

I. Partitioning as per Resource Availability: The number of disconnected components are likely to be more than the number of available resources or testers, hence each partition is likely to comprise of multiple disconnected components. The goal is to partition the components' weights in such a way that the achieved workload distribution is balanced, that is, the difference between the maximum and minimum weighted components is minimal. The scenario can be described as, let CompSet be the set of components $\{C_1; C_2; ::::; C_n\}$ with weights $\{W_{C1}; W_{C2}; ::::; W_{Cn}\}$. Create set of partitions PSet from the components in CompSet. The weight of each partition is the accumulation of the components in it, that is, for the set of partitions $\{P_1; P_2; ::::; P_k\}$ the weights are $\{W_{P1}; W_{P2}; ::::; W_{Pk}\}$. Distribute the components in CompSet among k partitions $\{P_1; P_2; ::::; P_k\}$ such that difference between $\max(W_{P1}; W_{P2}; ::::; W_{Pk})$ and $\min(W_{P1}; W_{P2}; ::::; W_{Pk})$ is minimal. The classic number partitioning problem can directly be reduced to this component partitioning problem and since the sizes of components could be different, balancing workload distribution is also NP-Hard. The present invention utilizes greedy technique to achieve the partitioning as shown in algorithm 2.

Algorithm 2 Balanced Partitioning

Figure 6:
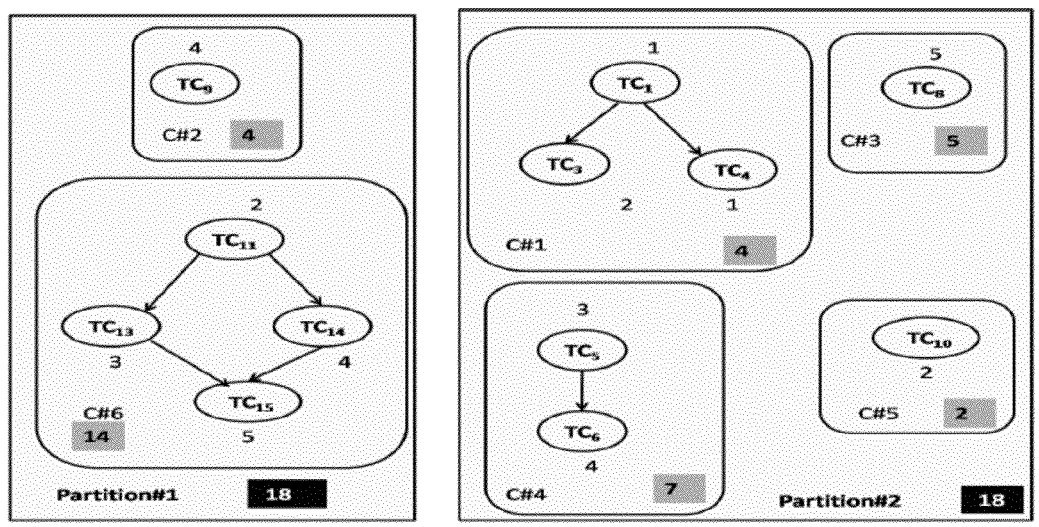
FIG. 6 represents balanced partitioning as per resource availability in accordance with one of the disclosed embodiment of the present invention.

Require: Comp: Set of components with their respective weights.
  N : Number of required partitions.
Ensure: PSet: Set of created partitions.
  BEGIN
  Sort CompSet in descending order.
  for i = 1 → N do:
    create partition $P_i$;
    $W_{P_i} \Leftarrow 0$;
    PSet ⇐ PSet ∪ {$P_i$};
  end for
  while CompSet! = ∅ do
    C ⇐ The component with largest weight $W_{C_{max}}$ in CompSet.
    If tie on $W_{C_{max}}$, component with least index in CompSet is chosen.
    $P_{min}$ ⇐ The partition with least weight $W_{min}$. If tie on $W_{min}$.
    partition with least index in CompSet is chosen.
    $P_{min} \Leftarrow P_{min} \cup \{C\}$;
    $W_{P_{min}} \Leftarrow W_{P_{min}} + W_{C_{max}}$;
    CompSet ⇐ CompSet − {C};
  end while
  END The complexity of the algorithm is O(n) where the number of components is n. The partitioning in FIG. 6 is achieved using this approach. However, apart from this algorithm, there have been various approaches known in the art to achieve balanced partitioning. The partition with the largest weight would define the total test execution cycle time. However, the other partitions will finish their workload earlier and hence remain idle for the remaining part of the test cycle. Consider the set of k partitions $\{P_1; P_2; ::::; P_k\}$ with the respective weights $\{W_{P1}; W_{P2}; ::::; W_{Pk}\}$. Let $W_{max}$ be the maximum weight in $\{W_{P1}; W_{P2}; ::::; W_{Pk}\}$ and total weight is $W = \sum_{i=1}^{k} W_{Pi}$.

Then the wait time is:

$$Waittime = \sum_{i=1}^{k}(W_{max} - W_{Pi})$$

and the utilization is:

$$\frac{totalweight(W)}{(no. of partitions \times testcycletime)} \times 100\%$$

i.e.

$$\frac{W}{(k * W_{max})} \times 100\%$$

For example, the idle time and utilization in the partitioning achieved in FIG. 6 are 0 time unit and 100% respectively.

b) Partitioning as per time constraint: In this case, the weight of each partition is bound by the specified time constraint from which the given deadline and the number of partitions are computed. The problem can be described as, for a given time constraint T create a set of k partitions PSet=$\{P_1; P_2; ::::; P_k\}$ such that the weights of the partitions are within the time constraint that is $W_{P1}; W_{P2}; ::::; W_{Pn} \leq T$. This problem can be reduced to a bin packing problem where the size of the bin is T and the partitions are created by filling the bins. Since bin packing is NP-Hard, the partitioning driven by time constraint is NP Hard as well. The first fit algorithm is used to solve this problem which is described in the Algorithm 3.

Algorithm 3 Time Aware Partitioning

```
Require: CompSet: Set of components with their respective
    weights. T : Time Constraint.
Ensure: PSet: Set of created partitions.
    BEGIN
    Sort CompSet in descending order.
    maxW ⇐ max({W_C1,W_C2,...,W_Cn}) ;
    if maxW > T then
        MESSAGE("NOT ENOUGH TIME") ;
        return;
    end if
    k ⇐ 0;
    while CompSet! = ∅ do
        k ⇐ k + 1;
        create partition P_k;
        W_Pk ⇐ 0;
        for i = 1 → |CompSet| do
            C ⇐ C_i;
            if (W_Pk + W_C) ≥ T then
                continue;
            end if
            P_k ⇐ P_k ∪ {C};
            W_Pk ⇐ W_Pk + W_c;
            CompSet ⇐ CompSet − {C};
        end for
        PSet ⇐ PSet ∪ {P_k};
    end while
    END
```

Figure 7:
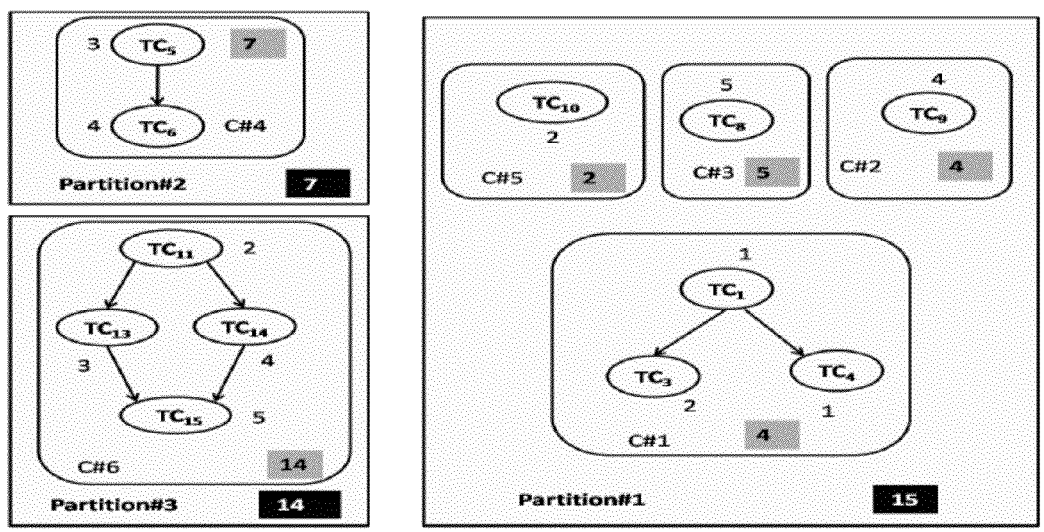
FIG. 7 represents balanced partitioning with a given time as a constraint in accordance with one of the disclosed embodiment of the present invention.

In this case for each partition it requires O(|CompSet|) traversals. Maximum number of partitions can be |CompSet| that is the number of the components. Hence the complexity of this algorithm is $O(n^2)$ where n=|CompSet|. The partitions for the time constraint T=15 are shown in FIG. 7.

If the given time for completing the test cycle is T and for the computed set of k partitions $\{P_1; P_2;:::;P_k\}$ with the respective weights $\{W_{P1}; W_{P2};::::; W_{Pk}\}$ then $$Idletime = \Sigma_{i=1}^{k}(T-W_i)$$

If the total weight is:

$$w = \Sigma_{i=1}^{k} w_{Pi}.$$

The utilization will be:

$$\frac{totalweight(W)}{(no. of partitions \times timeconstraint)} \times 100\%$$

i.e.

$$\frac{W}{(k*T)} \times 100\%$$

Note that, the utilization for resource availability based partitioning helps to decide on the number of testers and the utilization for time constraint based partitioning helps to decide on a logical deadline for a test cycle. For example, considering the workload distribution achieved in FIG. 7, the idle time is 9 unit and utilization is 80%.

BEST MODE/EXAMPLE OF WORKING OF THE INVENTION

The preceding description has been presented with reference to various embodiments of the invention. Persons skilled in the art and technology to which this invention pertains will appreciate that alterations and changes in the described structures and methods of operation can be practiced without meaningfully departing from the principle, spirit and scope of this invention.

Presented below are the experimental results on a set of industrial test project, varying time and resource constraints that show that either approach can be used for estimation as both the approaches produce similar results. First the number of available resources for testing and then the deadline time in discrete intervals is varied for study and analysis.

Experimental Set Up:

The experiment uses five ongoing projects from different domains as subjects. The projects chosen are long running projects that enabled the experimenters to observe practices followed across projects in different domains. All the projects chosen are web based applications and for all of them, testing is a manual process. The projects chosen are as follows:

BA: A core banking application
WUB: Web user behavior tracking application
FA: A financial service application
EC: An e-commerce application
HRMS: HRMS for a claims processing system Test teams classify test cases as simple, medium and complex based on the number of steps required to execute a test. The classification is then used to estimate the time required to design and create a new test case and the amount of time required to execute the same. For the selected projects, since these are long running, the resources and time estimates were refined over a period of time through experience gained from previous test cycles. The details of the test projects are shown in Table I.

TABLE 1

| Case Study | Regression test cases | Team Size | Regression Cycle (days) | Total hours |
|---|---|---|---|---|
| WUB | 261 | 2 | 10 | 93.8 |
| BA | 187 | 3 | 2 | 36 |
| FA | 98 | 3 | 5 | 94.2 |
| EC | 83 | 3 | 1.5 | 13 |
| HRMS | 50 | 2 | 3 | 22.8 |

Regression testing takes between 1.5 days to 10 days to complete with release cycle duration ranging from a fortnight to 3 months. Test cycles averages from one to four weeks and the regression suite is executed more than once during a release cycle. Changes and bug fixes are drivers to select subset of test cases for each test cycle. For the regression test the total hours depicted in Table I represent the total test execution time collected from test logs. This effort was spread over several days as indicated by the regression cycle column. The exact time spent by a tester each day was not recorded hence unavailable. The testers approximately spent between 3 hours to 6.25 hours/day testing. The rest of the day was spent on other activities—preparing reports and developing new test cases.

Test case dependencies and test execution times are provided by the project teams. However, the time waiting for dependent test cases to execute was not recorded and hence not available.

B. Experiment Design: The objectives of the experiments is to observe the following The cycle time and resource requirements identified by the workload distribution when the number of resources or the deadlines is specified respectively.
The overall idle time for the resources.

For the experiment, the complete regression test suite is considered for analysis, to be able to compare it with manual data. To gather data for the above, the experiment was carried out in two parts. First, the number of resources available are varied, to study its impact on total test execution time. The resources are varied from one to the total number of disconnected components, as that decides the maximum parallelization possible. Then the time constraint (deadline) is varied by one hour intervals from the maximum component weight to the total execution time for the entire test cases to observe the impact on the number of resources. For comparison with the earlier technique, only the highest utilization values are taken for each resource. Total idle time in each case is also computed. The results obtained from both the techniques are compared.

C. Results and Analysis:

TABLE 2

| Case Studies | No. of Disconnected Components | Weight of Distributed Components (min, max) minutes |
|---|---|---|
| WUB | 35 | 70, 260 |
| BA | 22 | 15, 300 |
| FA | 98 | 40, 75 |
| EC | 41 | 5, 170 |
| HRMS | 16 | 20, 655 |

The result of identification of disconnected components is presented in Table 2. In terms of dependencies, the number of disconnected components ranged from 8.42% to 100% across projects. BA project has 22 disconnected components with weights ranging from 15 minutes to 300 minutes. All the test cases in FA projects are independent; hence each test case is treated as a component.

TABLE 3

| No. of Resources | VR Total Time (Hours) | VD Total Time (Hours) | VR Idle Time (Hours) | VD Idle Time (Hours) |
|---|---|---|---|---|
| 1 | 93.80 | | 0.00 | |
| 2 | 46.90 | 47.33 | 0.00 | 0.67 |
| 3 | 31.40 | 32.34 | 0.40 | 2.92 |
| 4 | 23.90 | 24.34 | 1.80 | 3.50 |
| 5 | 19.10 | 19.34 | 1.60 | 2.42 |
| 6 | 15.80 | 16.33 | 1.20 | 4.17 |
| 7 | 13.70 | 14.33 | 1.80 | 6.50 |
| 8 | 12.10 | 12.33 | 2.80 | 4.83 |
| 9 | 10.50 | 11.33 | 0.70 | 7.42 |
| 10 | 10.00 | 10.33 | 6.20 | 8.67 |
| 11 | 8.80 | 9.33 | 2.40 | 8.83 |
| 12 | 8.40 | | 7.20 | |
| 13 | 7.90 | 8.33 | 9.10 | 14.50 |
| 14 | 7.40 | | 10.00 | |
| 15 | 7.40 | | 17.40 | |
| 16 | 7.30 | 7.33 | 23.50 | 23.50 |
| 17 | 7.00 | | 25.20 | |
| 18 | 5.60 | 6.33 | 6.70 | 20.17 |
| 19 | 5.50 | | 10.70 | |
| 20 | 5.50 | | 16.20 | |
| 21 | 5.00 | 5.33 | 11.20 | 18.17 |
| 22 | 5.00 | | 16.20 | |
| 23 | 4.80 | | 17.30 | |
| 24 | 4.40 | | 12.20 | |
| 25 | 4.30 | 4.33 | 14.50 | 14.50 |

Figure 8:
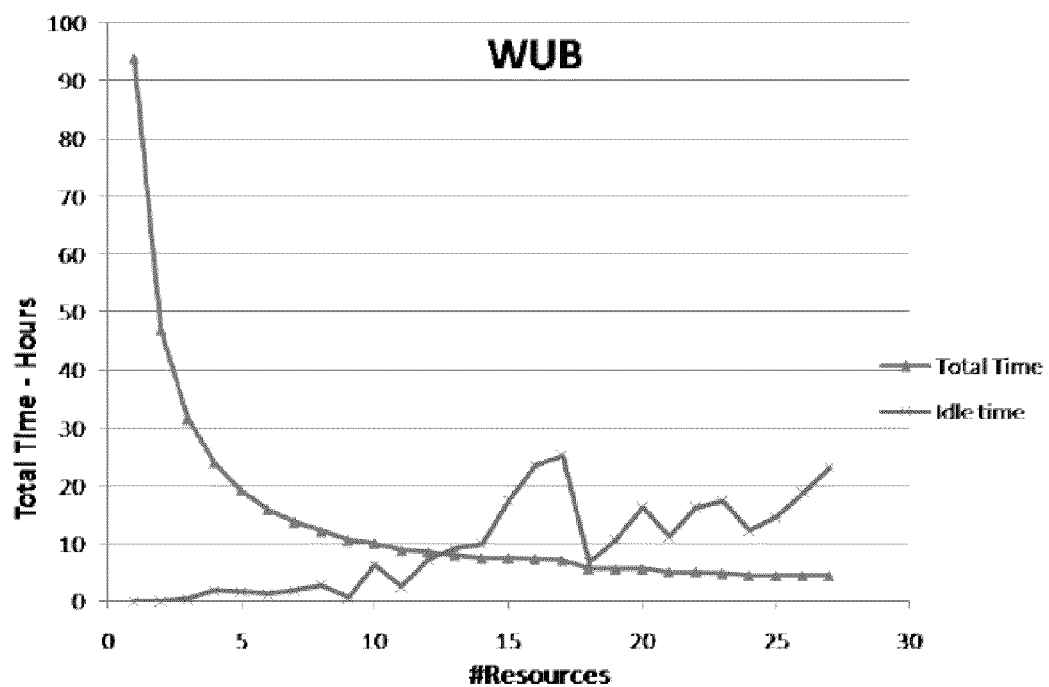
FIGS. 8(a), (b) and (c) is a graphical representation illustrating impact of varying resources on total execution time in accordance with one of the disclosed embodiments of the present invention.
Figure 8:
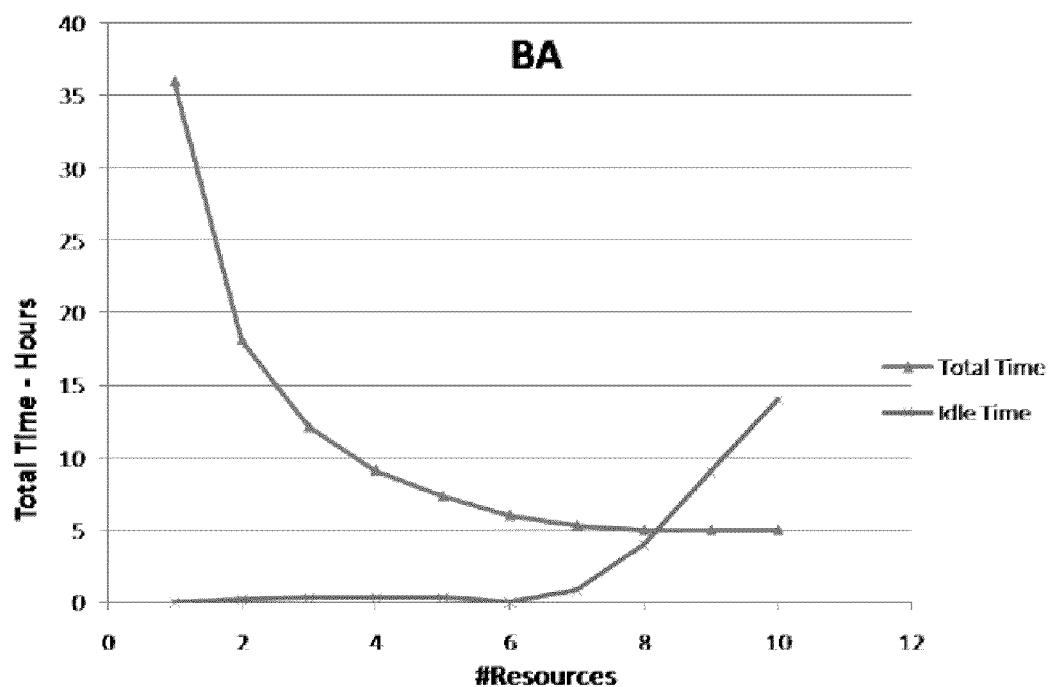
Figure 8:
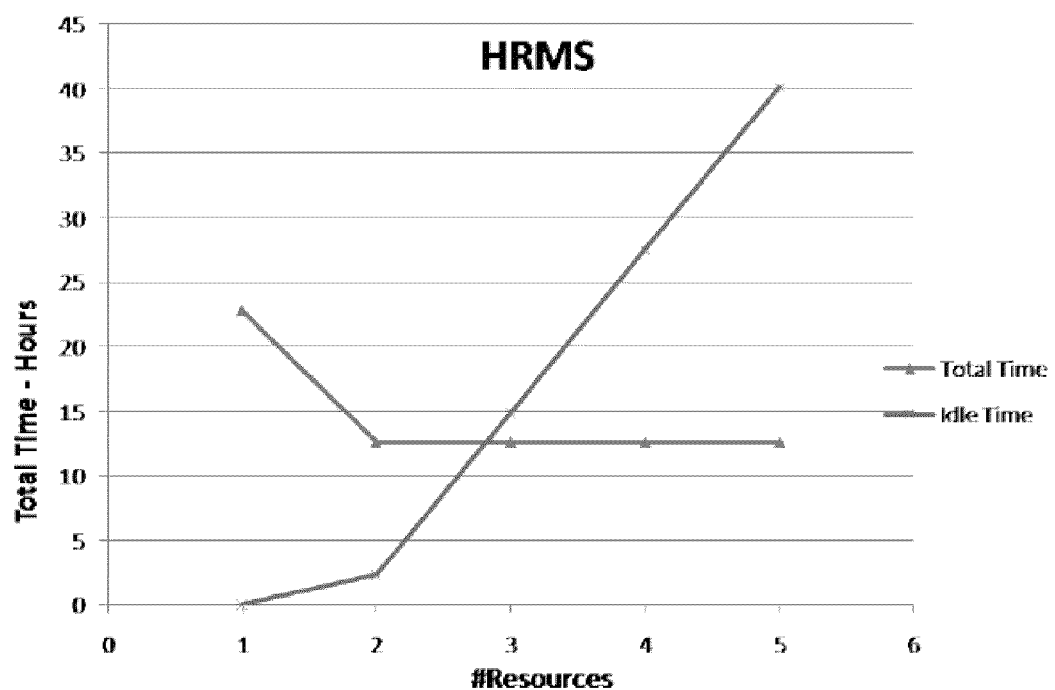
Figure 9:
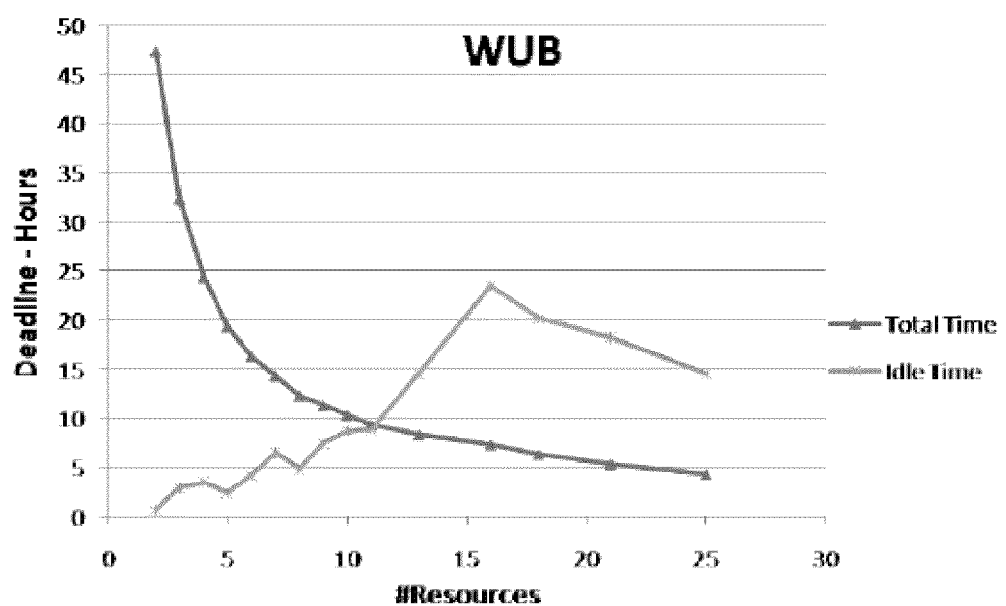
FIGS. 9 (a), (b) and (c) is a graphical representation illustrating impact of varying deadline on resources in accordance with one of the disclosed embodiments of the present invention.
Figure 9:
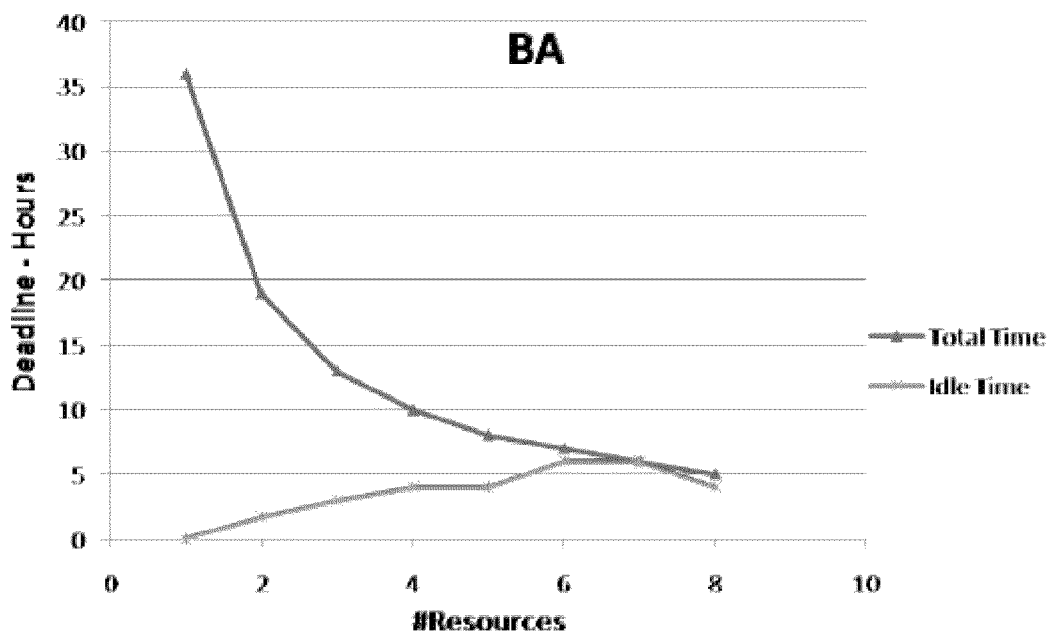
Figure 9:
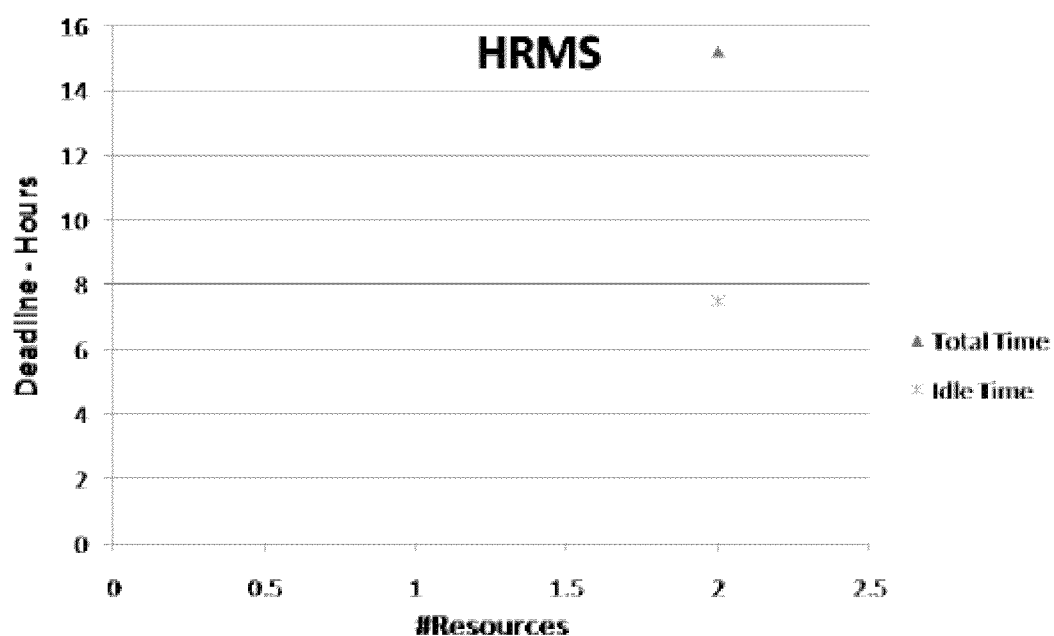

Varying Resource and Deadline: The results of varying the number of resources (VR) and varying the deadline (VD) in FIGS. 8 and 9 and Table 3. In Table 3 the impact of varying number of resources on total test execution time and the impact of varying deadline on number of resources for WUB project is shown. The corresponding idle time is also depicted. FIGS. 8 and 9 depict the data in Table 3 for WUB as well as BA and HRMS projects. The horizontal axis represents number of resources and the vertical axis represents the total test execution time/deadline and the corresponding idle time. Overall, FIGS. 8 (a), (b) and (c) shows the impact of varying number of resources on total test execution time and FIGS. 9 (a), (b) and (c) shows the impact of varying deadline on number of resources.

By increasing the resource count from 2 to 3 for WUB project, the testing can be completed in 31.40 hours and by doubling the number of resources, testing can be completed in 23.90 hours which can result in early completion by 33% and 49% with an effective utilization of 99.56% and 98.08%. It is observed that the maximum component size determines the effective execution time for a whole test suite. For HRMS project it is observed that weight of the largest disconnected component is greater than the half of the weight of the entire test suite. Hence this component influences the outcome of both the techniques. HRMS project therefore turned out to be an exception case where the effective execution time remains the same in spite of increasing resources and while varying time we see no increase in resources.

As seen in Table 3 the outcomes for both the techniques for WUB projects are comparable. For WUB, for up to 10 resources, both techniques produce outcomes that are within 5% of each other. As the number of resources increase, it is observed that in all cases the overall idle time increases as cycle time reduces resulting in effective utilization going down. This is the result of the difference in component weights, resulting in idle time while balancing the partitions. Applying more sophisticated techniques might provide better results when the resource count is high. The same behavior is observed for other projects as well with the first technique (varying resources) performing marginally better then second technique (varying deadline) for BA and EC projects. Both BA and EC have short test cycles.

D. Comparison with Actual Project Data:

In Table 4 the current project data with the outcome from both the techniques is compared. The project data as stated earlier is gathered from logs and does not include wait time nor does it guarantee if the workload is balanced. As seen from Table I, the testing activity is spread over several days. Using the first technique, for all projects except HRMS the outcome is comparable to the current project data. For HRMS case, a single large component, results in unbalanced workload which is reflected in the wait time. The project team confirmed the same. The second technique does not perform as well for all the projects with short test cycles—BA, EC and HRMS. For extremely short cycles resources utilization starts dropping very quickly.

TABLE 4

| Case Studies | Resources | Current Manual Time | VR Elapsed Time | VD Elapsed Time | % Diff Manual v/s VR | % Diff Manual v/s VD |
|---|---|---|---|---|---|---|
| WUB | 2 | 93.8 | 93.8 | 94.7 | 0.00% | 0.92% |
| BA | 3 | 36 | 36.3 | 39 | 0.83% | 8.33% |
| FA | 3 | 94.2 | 94.7 | 96.8 | 0.57% | 2.71% |
| EC | 3 | 13 | 13 | 14.5 | 0.00% | 11.46% |
| HRMS | 2 | 22.8 | 25.2 | 25.2 | 10.53% | 10.35% |

E. Threats to Validity:

Dependencies: For the experiment the test dependence information is gathered from the test team. It is observed that while the project teams is able to provide this information for larger test suites this activity may be time consuming and non trivial. Also, during maintenance, if changes are made to test cases that violate the dependency or introduce new dependencies, the same needs to be updated in the initial dependency information. It has been observed across several projects that regression suites are grouped together based on functionality. Tests for related functionality are usually grouped together. This might limit the impact of changes to dependencies to a particular module or physical component. Results would vary on the number of disjoint components identified and the component sizes.

Resource Constraints: Testers are usually familiar with certain functionality in the application and can only test the same. The same will have to be considered as a constraint when preparing work-plan. Resources availability fully or partly is another constraint that has been considered.

Change Spread: Changes are likely to be contained in particular functional modules and therefore to test components. This is important when selecting dependent test cases for subset of test cases in each cycle. If the changes are spread across the entire system, the approach will result in selecting large part of regression suite which will be similar to executing the entire test suite. The estimates for time and resources will however still be useful.

The approach of the present invention is simple, yet effective to parallelize testing and help test teams arrive at time and resource estimation using test dependencies and execution time. Experimental results on industrial projects, varying both time and resource constraints are presented that indicate technique compared well with the current manual project data, except for projects with short test cycles where the technique varying deadline did not perform as well. Both the techniques provide balanced workload distribution and help answer questions like how many resources are needed to meet a given deadline or how many days will it take to complete the test cycle with given number of resources and if any changes in either case and provide additional benefits. Using the present techniques, wait time for dependent test cases is eliminated.

The foregoing description of specific embodiments of the present invention has been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the claims appended hereto and their equivalents. The listing of steps within method claims do not imply any particular order to performing the steps, unless explicitly stated in the claim.

We claim:

1. A method of estimating constraints during execution of a plurality of test cycles, the method having computer executable code tangibly embodied on a non-transitory computer readable storage medium, and the method comprising:
   receiving, by a processor, constraints determining execution of the plurality of test cycles, wherein the constraints comprise resources and time, wherein a test cycle of the plurality of test cycles comprises a plurality of test cases, and wherein the test cycle indicates checking a functionality of an application;
   selecting, by the processor, a set of test cases from a test cycle;
   constructing, by the processor, a dependence graph for the set of test cases selected, wherein the dependence graph is constructed by:
   creating a plurality of nodes for the set of test cases; and
   creating an edge between two nodes of the plurality of nodes when a test case is executed subsequent to execution of a previous test case in the set of test cases;
   assigning, by the processor, a weight to a node of the plurality of nodes;
   constructing, by the processor, a dependence sub graph based on the dependence graph for the set of test cases selected, wherein the dependence sub graph is constructed by performing a depth first walk on the dependence graph of the set of test cases selected;
   identifying, by the processor, a subset of nodes based on the dependence sub graph, wherein the subset of nodes indicates absence of the edge for the node with previous or subsequent node;
   grouping, by the processor, the subset of nodes into a first group and a second group based on the constraints and the dependence sub graph;
   calculating, by the processor, a first aggregate weight and a second aggregate weight corresponding to the first group and the second group respectively;
   rearranging, by the processor, the nodes in the first group and in the second group to balance the first aggregate weight and the second aggregate weight, wherein the nodes are rearranged to have a minimum difference between the first aggregate weight and the second aggregate weight corresponding to the first group and the second group respectively; and
   executing, by the processor, the subset of the nodes in the first group and the second group for the constraints received for estimating the constraints required to execute the test cycle.

2. The method of claim 1, wherein the weight indicates a time the test case takes to execute a task to check the functionality.

3. The method of claim 1, wherein the plurality of test cases are selected based on dependency amongst the plurality of test cases for executing the the test cycle and parameters to modify errors during the execution of the test cycle.

4. The method of claim 1, wherein the dependency sub graph is constructed by traversing through the plurality of test cases in the dependency graph to identify dependencies across the plurality of test cases.

5. The method of claim 1, wherein the first aggregate weight and the second aggregate weight are calculated by adding the weight of each node in the first group and the second group respectively.

6. The method of claim 1, wherein the subset of nodes are grouped by changing the resources and the time, wherein the resources are changed when the resources are constraint, and wherein the time is changed when the resources are constraint.

7. The method of claim 1, wherein the subset of nodes are grouped using a greedy technique with the resource as the constraint.

8. The method of claim 1, further comprising computing a wait time for the test cycle based on the first aggregate weight and the second aggregate weight with the resource as the constraint.

9. The method of claim 1, further comprising computing an efficiency based on the estimation of the constraints, wherein the efficiency is computed based on the first aggregate weight and the second aggregate weight and the time for executing the test cycle.

10. The method of claim 1, wherein the subset of nodes are grouped using a bin packing technique with the time as the constraint.

11. The method of claim 1, further comprising computing a wait time for the test cycle based on the first aggregate weight and the second aggregate weight with the time as the constraint.

12. A system for estimating constraints during execution of a plurality of test cycles, the system comprising:
a memory; and
a processor coupled to the memory, wherein the processor executes program instructions stored in the memory to;
receive constraints determining execution of the plurality of test cycles, wherein the constraints comprise resources and time, wherein a test cycle of the plurality of test cycles comprises a plurality of test cases, and wherein the test cycle indicates checking a functionality of an application;
select a set of test cases from a test cycle;
construct a dependence graph for the set of test cases selected, wherein the dependence graph is constructed by:
create a plurality of nodes for the set of test cases; and
create an edge between two nodes of the plurality of nodes when a test case is executed subsequent to execution of a previous test case in the set of test cases;
assign a weight to each of the plurality of nodes;
construct a dependence sub graph based on the dependence graph for the set of test cases selected, wherein the dependence sub graph is constructed by performing a depth first walk on the dependence graph of the set of test cases selected;
identify a subset of nodes based on the dependence sub graph, wherein the subset of nodes indicates absence of the edge for the node with previous or subsequent node;
group the subset of nodes into a first group and a second group based on the constraints and the dependence sub graph;
calculate a first aggregate weight and a second aggregate weight corresponding to the first group and the second group respectively;
rearrange the nodes in the first group and in the second group to balance the first aggregate weight and the second aggregate weight, wherein the nodes are rearranged to have minimum difference between the first aggregate weight and the second aggregate weight corresponding to the first group and the second group respectively; and
execute the subset of the nodes in the first group and the second group for the constraints received for estimating the constraints required to execute the test cycle.

13. The system of claim 12, wherein the processor computes a wait time and an efficiency based on the estimation of the constraints in the test cycle.

14. The system of claim 12, wherein the subset of nodes are grouped using a greedy technique with resource as the constraint.

15. The system of claim 12, wherein the subset of nodes are grouped using a bin packing technique with time as the constraint.

* * * * *